United States Patent [19]

Baer et al.

[11] Patent Number: 5,351,121
[45] Date of Patent: Sep. 27, 1994

[54] SOLID-STATE LASER FOURIER-TRANSFORM RAMAN SPECTROMETER

[75] Inventors: Thomas M. Baer; Kelly A. Cox; Phillip Gooding, all of Mountain View; John Cole, Sunnyvale; David F. Head, Los Gatos; Gregory J. Kintz, Mountain View, all of Calif.

[73] Assignee: Spectra-Physics Laser Diode Systems, Mountain View, Calif.

[21] Appl. No.: 9,454

[22] Filed: Jan. 27, 1993

[51] Int. Cl.[5] .......................... G01N 21/65; G01J 3/44
[52] U.S. Cl. .................................................. 356/301
[58] Field of Search ................................ 356/301, 346

[56] References Cited

U.S. PATENT DOCUMENTS 3,914,055 10/1975 Wolga et al. ..................... 356/301

Primary Examiner—F. L. Evans
Attorney, Agent, or Firm—Haynes & Davis

[57] ABSTRACT

A Fourier Transform Raman Spectrometer system includes a folded V laser cavity. A first leg of the folded V laser cavity is defined by a highly reflective end mirror and a dichroic fold mirror and a second leg of the folded V laser cavity is defined by the fold mirror and an output coupler. A solid-state laser gain medium is disposed in the first leg of the folded V laser cavity and is pumped by a pump source aligned with the optical path of the first leg of the laser cavity and radiating through the fold mirror. The fold mirror is highly transmissive at the wavelength of pump radiation from the pump source and highly reflective at the laser output wavelength. An output beam from the laser is passed through a tuneable filter comprising an acousto-optic device and is directed at a sample to be analyzed. Light reflected from the sample is directed to a Raman Spectrometer for analysis.

10 Claims, 2 Drawing Sheets

SOLID-STATE LASER FOURIER-TRANSFORM RAMAN SPECTROMETER

BACKGROUND OF THE INVENTION

1. Field Of The Invention

The present invention relates to Fourier-Transform (FT) Raman spectroscopy. More particularly, the present invention relates to a solid-state laser Fourier-Transform Raman spectrometer.

2. The Prior Art

A traditional FT Raman spectrometer incorporates a near-infrared Nd:YAG laser, a narrow bandwidth spectral filter for reducing spurious light from the laser, and a series of attenuators to adjust the laser output power over a wide range. The laser output is directed on to a sample and the light scattered from the sample is collected and the frequency content of the scattered light is analyzed.

The Raman emission is typically at very low light levels: roughly $1 \times 10^{-8}$ of the incident power. Thus the FT Raman apparatus is very sensitive to spurious emission from the laser and to laser amplitude noise. One of the most common sources of spurious laser emission is the non-lasing fluorescent emission from the laser active medium and scattered light from the arc lamp or diode pump sources which are used to drive the laser. There are several strong emission lines located close enough to the desired laser line in Nd:YAG and it is thus difficult to remove them by filtering, with the result that they show up as spurious Raman signals. Common techniques to suppress these spurious signals are the use of dispersive elements such as grating or the use of absorbing interference filters. Both of these approaches tend to attenuate the laser beam by 50% to 75%, thus increasing the total amount of laser power required from the source.

The Raman spectrum is sensitive to fluctuations in the laser amplitude and wavelength. Fluctuations in laser amplitude will show up directly as noise on the Raman signal. Fluctuations in laser frequency will show up as noise in the location of the Raman line center. Unfortunately, the act of directing the laser onto a sample that scatters the incident light can increase the laser amplitude and frequency noise due to feedback of scattered light to the source laser.

One of the limiting factors in the frequency resolution of the FT Raman approach is the intrinsic linewidth of the laser system. Most diode pumped solid state lasers have emissions consisting of several longitudinal modes extending over several cm (about 50 GHz). This broadband emission often limits the achievable instrumental resolution.

Different samples have different Raman cross sections so it is necessary to attenuate the laser intensity to adjust the incident light to an appropriate level. Often this is done by turning down the drive power to the arc lamp or laser diode powering the laser source. Turning down the pump power has the negative side effects of changing the laser beam spatial profile, changing the emission direction of the laser beam, and altering the spectral profile of the emitting laser. All of these changes can impact the performance of the FT Raman instrument. Alternatively, neutral density filters that absorb or reflect a certain fraction of the laser power can be used which are mechanically inserted and removed as necessary. This approach requires the use of complicated moving parts which are subject to failure and relies on the attenuation of the neutral density filters remaining constant with time.

It is therefore an object of the present invention to provide a Fourier Transform Raman Spectrometer system which avoids or reduces these problems inherent in present systems.

BRIEF DESCRIPTION OF THE INVENTION

A Fourier Transform Raman Spectrometer system according to the present invention comprises a laser producing an output emission along an optical path, a tuneable filter comprising an acousto-optic device disposed along the optical path and positioned so as to intersect an output beam from the laser, means for tuning the tuneable filter to a narrow band of colors around a selected laser emission line of radiation from the laser, means for disposing a sample to be analyzed in a path of the output beam from the tuneable filter; and a raman spectrometer positioned to receive light reflected from the sample.

A Fourier Transform Raman Spectrometer system according to a preferred embodiment of the present invention includes a folded V laser cavity. A first leg of the folded V laser cavity is defined by a highly reflective end mirror and a dichroic fold mirror and a second leg of the folded V laser cavity is defined by the fold mirror and an output coupler. A solid-state laser gain medium is disposed in the first leg of the folded V laser cavity and is pumped by a pump source aligned with the optical path of the first leg of the laser cavity and radiating through the fold mirror. The fold mirror is highly transmissive at the wavelength of pump radiation from the pump source and highly reflective at the laser output wavelength. An output beam from the laser is passed through a tuneable filter comprising an acousto-optic device and is directed at a sample to be analyzed. Light reflected from the sample is directed to a Raman Spectrometer for analysis.

DETAILED DESCRIPTION OF A PREFERRED EMBODIMENT

Those of ordinary skill in the art will realize that the following description of the present invention is illustrative only and not in any way limiting. Other embodiments of the invention will readily suggest themselves to such skilled persons.

Figure 1:
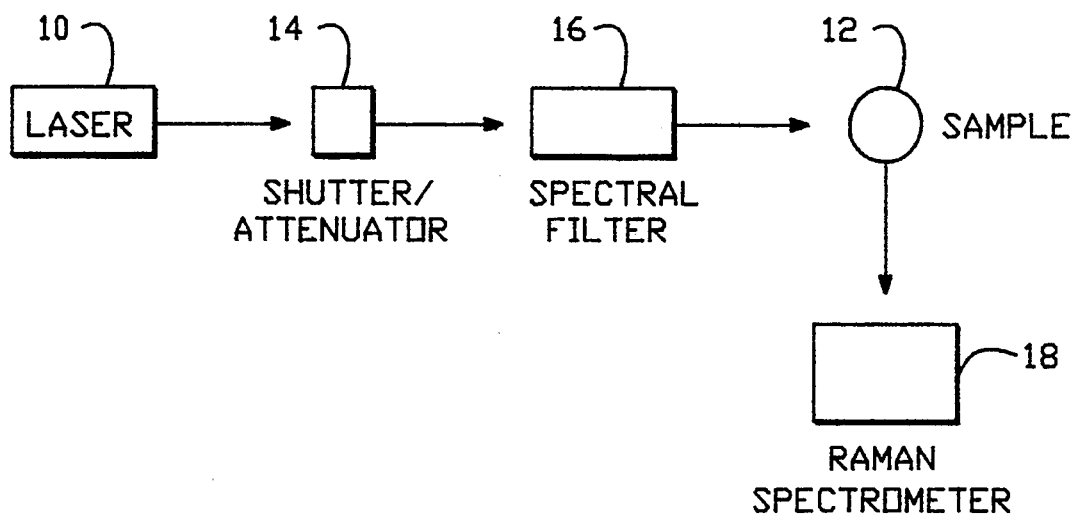
FIG. 1 is a block diagram of a typical prior art FT laser Raman spectrometer device.

Referring first to FIG. 1, a block diagram of a typical prior-art FT Raman Spectrometer is shown. Radiation from laser 10 is directed at a sample 12 through shutter-/attenuator 14 and spectral filter 16. Radiation reflected from sample 12 is gathered by Raman Spectrometer 18.

The prior-art FT Raman Spectrometer of FIG. 1 is susceptible to the problems noted herein. Spurious laser emission and scattered pump radiation can provide false signals which affect the analysis. In addition, the problems of attenuation for different samples also negatively affects measurement accuracy.

Figure 2A:
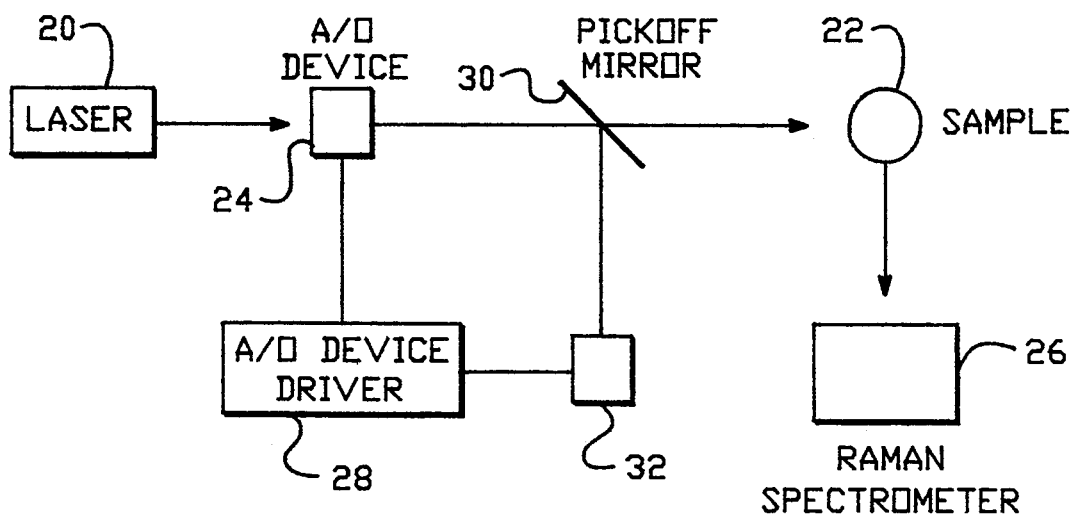
FIG. 2a is a block diagram of a FT laser Raman spectrometer according to a presently preferred embodiment of the invention.

The FT Raman Spectrometer system of the present invention addresses all of the shortcomings of the prior art systems noted above. Referring now to FIG. 2a, a block diagram of a FT Raman Spectrometer according to the present invention is shown. Radiation from laser 20 is directed at a sample 22 through acousto-optic (AO) device 24. Radiation reflected from sample 22 is gathered by Raman Spectrometer 26. AO device 24 is controlled by AO device driver 28.

The preferred laser medium is Nd:YVO4, which has much lower fluorescence than Nd:YAG in the band near the laser line. A preferred AO device is a Model N48029-1.06 AO Tuneable Filter, available from Neos Technologies of Melbourne, Fla., or a Model TEAF-90-1.2S, available from Brimrose Corporation of America, of Baltimore, Md. AO device driver 28 may be a Model No. N64040-100-1AMVCO Acousto-optic Driver from Neos Technologies, Inc. of Melbourne, Fla.

The AO device 24 can also be used to control the laser intensity by changing the power level of the RF applied to it by the AO device driver 28. In this manner the laser can be varied from essentially zero (no RF applied to the AO device 24), eliminating the need for a mechanical shutter, to over 90% of the total available power from the laser (approximately 2 W of RF power applied to the AO device 24). The AO device 24 requires no mechanical devices and, since the laser is not adjusted directly, there is no change in the laser emission characteristics over this large dynamic range. With this intensity control we can also design a servo loop which automatically maintains the laser output power at a chosen level and substantially reduces the laser amplitude noise. To further reduce fluorescent and pump light from reaching the sample an acousto-optic device is employed as a very efficient tunable filter in the beam train. This device uses an acousto-optic crystal to set up a variable diffraction grating. In contrast to normal gratings, this AO diffraction grating is only efficient at one wavelength which is determined by the frequency of the applied RF. Light not diffracted by the AO device passes through undeflected. A simple aperture can be used to discriminate against the undiffracted light. In the FT Raman system, the RF applied to the tunable AO filter is adjusted to that the laser beam is efficiently diffracted. Typical diffraction efficiencies can exceed 90%. The non-lasing light (both pump light and fluorescence) is not diffracted and is easily separated from the laser emission.

The light diffracted by AO device 24 is shifted slightly in frequency by the AO crystal and does not cause amplitude noise if it is scattered back to the laser. Thus the addition of the AO device 24 in the beam train substantially reduces the sensitivity of the laser to radiation scattered back by the Raman sample.

As shown in FIG. 2a, AO device 24 may be controlled by AO device driver 28 in a servo loop in order to automatically maintain the output power delivered to sample 22 by laser 20 at a chosen level and thereby substantially reduce the laser amplitude noise. This is accomplished by employing a pickoff mirror 30 to direct light to a detector/signal conditioner 32. The output of detector/signal conditioner 32 is used to control the AO device driver 28.

Figure 2B:
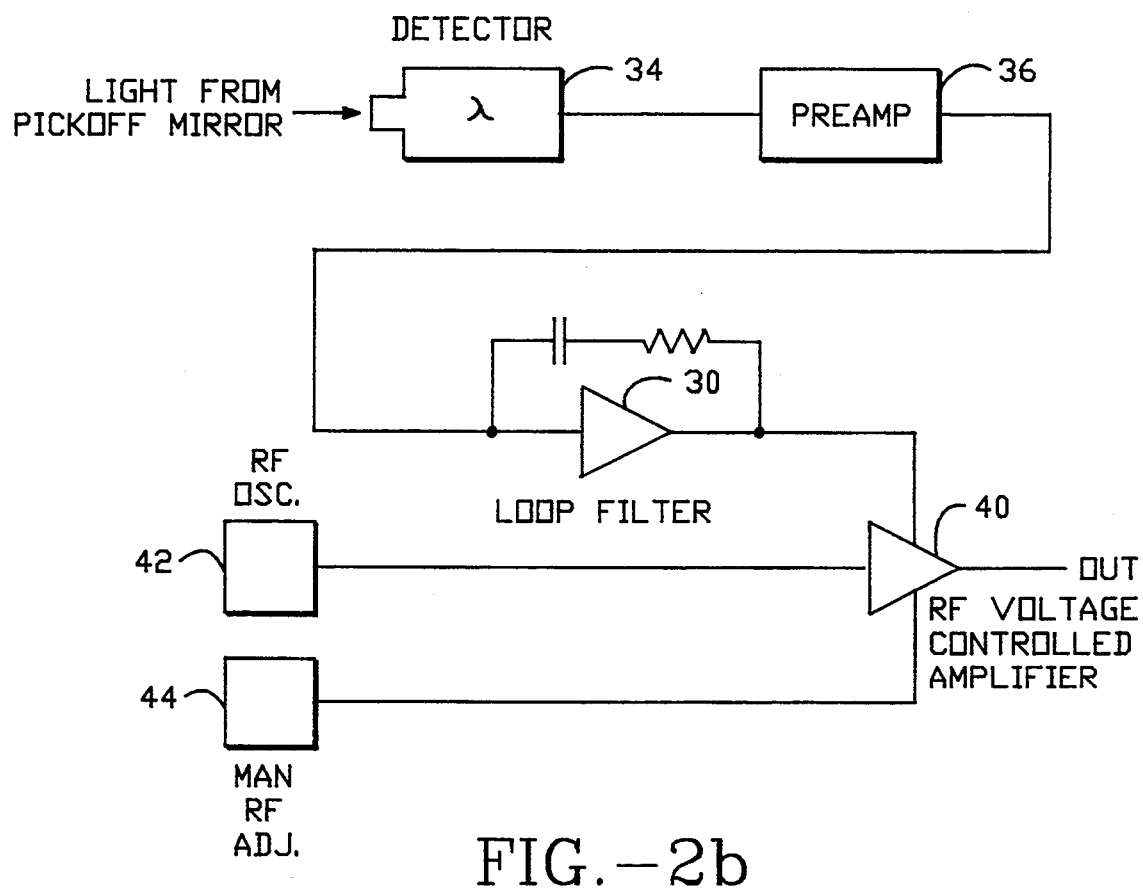
FIG. 2b is a block diagram of a typical AO device driver and detector/signal conditioner suitable for use in the present invention.

Referring now to FIG. 2b, a block diagram of a typical AO device driver 28 and detector/signal conditioner 32 is shown. Light from pickoff mirror 30 is directed photodetector 34, which may be a Model SGD-200 Photodetector from EGG Optoelectronics in Vaudreuil, P.Q. Canada. The signal from photodetector 34 is amplified by preamplifier 36 and then passed to loop filter 38, comprising an amplifier and bandpass filters as is apparent to those of ordinary skill in the art of servo design. The purpose of loop filter 38 is to provide the electronic circuitry necessary to opitimize the performance of the intensity servo loop. The output of loop filter 38 is used to control voltage-controlled RF amplifier 40, such as a Model N21080-1 SAS from Neos Technologies, Inc. of Melbourne Fla., driven from an RF oscillator 42 at a frequency of about between 40 and 100 MHz. A manual RF output adjustment is provided by Manual RF Adjust 44.

Figure 3:
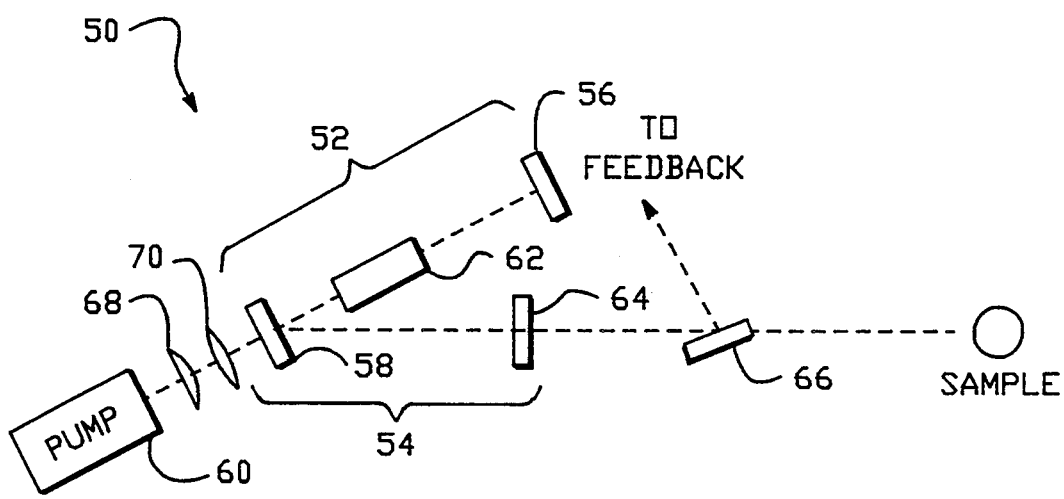
FIG. 3 is a block diagram of a folded laser cavity arrangement preferred for use in the FT laser Raman spectrometer of the present invention.

According to a presently preferred embodiment of the invention, and as may be seen with reference to FIG. 3, laser cavity 50 comprises a folded V cavity having a first leg 52 and a second leg 54. First leg 52 is defined by highly reflective end mirror 56 and fold mirror 58. End mirror 56 is coated to be highly reflective at the lasing wavelength and comprises a flat substrate. Fold mirror 58 is coated to be highly transmissive at the pump radiation wavelength and highly reflective at the lasing wavelength and may also comprise a flat substrate to allow coupling of pump radiation from pump source 60 into first leg 52 to excite solid state gain media 62 located therein. In a presently preferred embodiment of the invention, pump source 60 may be a fiber-coupled laser diode bar such as the one disclosed in U.S. Pat. No. 5,127,068 and solid state gain medium 62 may be a 4×4×4 mm Nd:YV04 crystal located 10 mm from the fold mirror 58. The distance from the other end of solid state gain medium 62 to highly reflective end mirror 56 is 86 mm.

Second leg 54 of laser cavity 50 is disposed at an acute angle from first leg 52 (an angle of 20° has been used) and is defined by fold mirror 58 and output coupler 64, having a 9% transmissivity, a 4.0 meter radius of curvature and a diameter of 1 cm, and may be located 76 mm from fold mirror 58.

A pickoff mirror 66, which may comprise a wedged flat substrate with a 1% reflectivity coating on one surface and an anti-reflective coating on the other surface, is aligned in the beam path outside of the output coupler and is used to supply the optical feedback signal to the circuit of FIG. 2b. Pump radiation is directed through collimating lens 68 having a focal length of 40 mm and a diameter of 20 mm, and focussing lens 70, having a focal length of 20 mm and a diameter of 21 min.

The use of a folded cavity design allows orienting the pump source 60 in alignment with the fold mirror 58 so that the pump radiation is not emitted directly through the output coupler 64 where it might be collected and focussed on the sample. The folded V geometry allows the active medium 62 to be placed in the center of the laser cavity, thus reducing the laser emission to only two or three longitudinal modes and a total linewidth of less than 0.1 cm$^{-1}$.

The system disclosed herein addresses all of the short comings mentioned above. We have chosen Nd:YV0$_4$ as the active medium which has been measured to have much lower fluorescence than Nd:YAG in the band near the laser line. (See Graphs). The folded 'V' cavity 50 with the diode pump radiation directed down the first leg 52 of the V opposite that of the output coupler 64 in second leg 54. Thus the pump radiation is not emitted directly out the output coupler 64 where it might be collected and focussed on the sample. The V geometry allows the active medium to be placed in the center of the laser cavity, thus reducing the laser emission to only two or three longitudinal modes and a total linewidth of less than 0.1 cm$^{-1}$.

To further reduce fluorescent and pump light from reaching the sample we employ an AO device 24 in the beam train that acts as a very efficient tunable filter. As previously mentioned, this device uses an acousto-optic (AO) crystal to set up a variable diffraction grating. In contrast to normal gratings, this AO diffraction grating is only efficient at one wavelength which is determined by the frequency of the applied RF. Light not diffracted by the AO device passes through undeflected. A simple aperture can be used to discriminate against the undiffracted light. In the FT Raman system of the present invention, the RF applied to the tunable AO device 24 is adjusted to that the laser beam is efficiently diffracted. Typical diffraction efficiencies can exceed 90%. The non-lasing light (both pump light and fluorescence) is not diffracted and is easily separated from the laser emission.

The light diffracted by AO device 24 is shifted slightly in frequency by the AO crystal and does not cause amplitude noise if it is scattered back to the laser. Thus the addition of the AO device in the beam train reduces substantially the sensitivity of the laser to radiation scattered back by the Raman sample.

Moreover, the AO device 24 can also be used to control the laser intensity by changing the power level of the RF applied to the AO device 24. In this manner the laser can be varied from essentially zero (no RF applied to the AO device 24), eliminating the need for a mechanical shutter, to over 90% of the total available power from the laser (approximately 2 watts of RF power applied to the AO crystal). This "volume control" requires no mechanical devices and, since the laser is not adjusted directly, there is no change in the laser emission characteristics over this large dynamic range. With this intensity control we can also design a servo loop which automatically maintains the laser output power at a chosen level and substantially reduces the laser amplitude noise.

While embodiments and applications of this invention have been shown and described, it would be apparent to those skilled in the art that many more modifications than mentioned above are possible without departing from the inventive concepts herein. The invention, therefore, is not to be restricted except in the spirit of the appended claims.

What is claimed is:

1. A Fourier Transform Raman Spectrometer system comprising:
    a laser producing an output emission along an optical path;
    a tuneable filter comprising an acousto-optic device disposed along said optical path and positioned so as to intersect an output beam from said laser;
    means for tuning said tunable filter to a narrow band of colors around a selected laser emission line of radiation from said laser;
    means for disposing a sample to be analyzed in a path of said output beam from said tuneable filter; and
    a raman spectrometer positioned to receive light scattered from said sample.

2. The Fourier Transform Raman Spectrometer system of claim 1 wherein a solid-state laser gain medium is centered in a cavity defining said laser.

3. The Fourier Transform Raman Spectrometer system of claim 2 wherein said solid-state laser gain medium is Nd:YVO$_4$.

4. The Fourier Transform Raman Spectrometer system of claim 1 wherein said means for tuning includes means for selectively attenuating the output power of said selected laser emission line.

5. The Fourier Transform Raman Spectrometer system of claim 1 wherein said tuning means employs feedback means for controlling the output power of said narrow band of colors around said selected laser emission line.

6. A Fourier Transform Raman Spectrometer system comprising:
    a folded V laser cavity comprising a first leg defined by a highly reflective end mirror and a dichroic fold mirror and a second leg defined by said fold mirror and an output coupler, said cavity including an optical path therethrough;
    a solid-state laser gain medium disposed in said optical path in said first leg of said cavity;
    a pump source disposed outside said cavity and aligned with said fold mirror and said optical path in said first leg of said cavity;
    a tuneable filter comprising an acousto-optic device disposed outside said cavity along said optical path and positioned so as to intersect an output beam from said second leg of said cavity;
    means for tuning said tunable filter to a narrow band of colors around a selected laser emission line of radiation from said laser;
    means for disposing a sample to be analyzed in a path of said output beam from said tuneable filter; and
    a Raman Spectrometer positioned to receive light scattered from said sample.

7. The Fourier Transform Raman Spectrometer system of claim 6 wherein said solid-state laser gain medium is centered in said cavity.

8. The Fourier Transform Raman Spectrometer system of claim 6 wherein said solid-state laser gain medium is Nd:YVO$_4$.

9. The Fourier Transform Raman Spectrometer system of claim 6 wherein said means for tuning includes means for selectively attenuating the output power of said selected laser emission line.

10. The Fourier Transform Raman Spectrometer system of claim 6 wherein said tuning means employs feedback means for controlling the output power of said selected laser emission line.

* * * * *